(12) United States Patent
Zhou et al.

(10) Patent No.: US 10,709,394 B2
(45) Date of Patent: Jul. 14, 2020

(54) METHOD AND SYSTEM FOR 3D RECONSTRUCTION OF X-RAY CT VOLUME AND SEGMENTATION MASK FROM A FEW X-RAY RADIOGRAPHS

(71) Applicant: Siemens Healthcare GmbH, Erlangen (DE)

(72) Inventors: Shaohua Kevin Zhou, Plainsboro, NJ (US); Sri Venkata Anirudh Nanduri, College Park, MD (US); Jin-hyeong Park, Princeton, NJ (US); Haofu Liao, Rochester, NY (US)

(73) Assignee: Siemens Healthcare GmbH, Erlangen (DE)

( * ) Notice: Subject to any disclaimer, the term of this patent is extended or adjusted under 35 U.S.C. 154(b) by 248 days.

(21) Appl. No.: 15/871,531

(22) Filed: Jan. 15, 2018

(65) Prior Publication Data

US 2019/0216409 A1  Jul. 18, 2019

(51) Int. Cl.
| | |
|---|---|
| G06T 7/00 | (2017.01) |
| G06T 7/30 | (2017.01) |
| A61B 5/00 | (2006.01) |
| A61B 6/03 | (2006.01) |
| G06T 7/11 | (2017.01) |
| G06T 11/00 | (2006.01) |
| A61B 6/00 | (2006.01) |
| G06T 5/00 | (2006.01) |

(52) U.S. Cl.
CPC ............... *A61B 6/032* (2013.01); *A61B 6/52* (2013.01); *G06T 7/0012* (2013.01); *G06T 7/11* (2017.01); *G06T 11/003* (2013.01); *G06T 11/005* (2013.01); *G06T 5/005* (2013.01); *G06T 2200/04* (2013.01); *G06T 2207/10081* (2013.01); *G06T 2207/30004* (2013.01)

(58) Field of Classification Search
CPC ......... A61B 5/7267; A61B 6/032; G06T 7/30; G06T 2207/20081; G06T 7/11
See application file for complete search history.

(56) References Cited

U.S. PATENT DOCUMENTS

| | | | |
|---|---|---|---|
| 6,944,261 | B2 | 9/2005 | Adachi et al. |
| 7,327,822 | B2 | 2/2008 | Sauer et al. |
| 7,551,708 | B2 | 6/2009 | Kumar et al. |
| 9,495,770 | B2 | 11/2016 | Noo |
| 9,760,807 | B2 | 9/2017 | Zhou et al. |

(Continued)

FOREIGN PATENT DOCUMENTS

WO  WO2012017345 A1  2/2012

OTHER PUBLICATIONS

Extended European Search Report (EESR) dated Jul. 16, 2019 in corresponding European Patent Application No. 19151550.1.

(Continued)

*Primary Examiner* — Don K Wong

(57) ABSTRACT

A method and apparatus for automated reconstruction of a 3D computed tomography (CT) volume from a small number of X-ray images is disclosed. A sparse 3D volume is generated from a small number of x-ray images using a tomographic reconstruction algorithm. A final reconstructed 3D CT volume is generated from the sparse 3D volume using a trained deep neural network. A 3D segmentation mask can also be generated from the sparse 3D volume using the trained deep neural network.

20 Claims, 5 Drawing Sheets

(56) References Cited

U.S. PATENT DOCUMENTS

| | | | |
|---|---|---|---|
| 2009/0175523 A1 | 7/2009 | Chen et al. | |
| 2016/0133033 A1 | 5/2016 | Brady et al. | |
| 2017/0200067 A1 | 7/2017 | Zhou et al. | |
| 2017/0277981 A1 | 9/2017 | Zhou et al. | |
| 2017/0337682 A1* | 11/2017 | Liao | G06T 7/30 |

OTHER PUBLICATIONS

Zhang, Hanming et al: "Image Prediction for Limited-angle Tomography via Deep Learning with Convolutional Neural Network"; Jul. 29, 2016.

Stephan Antholzer et al: "Deep Learning for Photoacoustic Tomography from Sparse Data"; arxiv.org; Cornell University Library; 201 Olin Library Cornell University Ithaca; NY 14853; Apr. 15, 2017; pp. 1-22.

McCann, Michael et al: "Convolutional Neural Networks for Inverse Problems in Imaging: A Review"; IEEE Signal Processing Magazine; vol. 34; No. 6; Nov. 1, 2017; pp. 85-95.

Zheng et al., "3D Reconstruction of a Patient-Specific Surface Model of the Proximal Femur from Calibrated X-ray Radiographs: A Validation Study," Medical Physics; 2009; pp. 1155-1166.

Zheng et al., "Scaled, Patient-Specific 3D Vertebral Model Reconstruction Based on 2D Lateral Fluoroscopy," International Journal of Computer Assisted Radiology and Surgery; 2011; pp. 351-366.

Baka et al., "2D-3D Shape Reconstruction of the Distal Femur from Stereo X-Ray Imaging Using Statistical Shape Models," Medical Image Analysis; 2011; pp. 840-850.

Schumann et al., "An Integrated System for 3D Hip Joint Reconstruction from 2D X-Rays: A Preliminary Validation Study," Annals of Biomedical Engineering; 2013; pp. 2077-2087.

Yu et al., "Fully Automatic Reconstruction of Personalized 3D Volumes of the Proximal Femur from 2D X-Ray Images," International Journal of Computer Assisted Radiology and Surgery; 2015; pp. 1673-1685.

Jin et al., "Deep Convolutional Neural Network for Inverse Problems in Imaging," IEEE Transactions on Image Processing; vol. 26; No. 9; Sep. 2017; pp. 4509-4522.

* cited by examiner

3D Segmentation Mask

METHOD AND SYSTEM FOR 3D RECONSTRUCTION OF X-RAY CT VOLUME AND SEGMENTATION MASK FROM A FEW X-RAY RADIOGRAPHS

BACKGROUND OF THE INVENTION

The present invention relates to automated reconstruction of a 3D computed tomography (CT) volume from 2D X-ray radiographs, and more particularly, to automated reconstruction of a 3D CT volume and a 3D segmentation mask from a small number of X-ray radiographs.

X-ray computed tomography (CT) is widely used for obtaining images of different parts of the body which are more detailed than standard X-rays. In computed tomography, many X-ray images are taken from various angles. All of these X-ray images are then processed using a tomographic reconstruction algorithm to generate the 3D CT volume data, which can then be view as images in the axial, coronal, sagittal planes.

CT is regarded as a moderate to high radiation diagnostic technique. Moreover, acquiring a CT scan is more time consuming and expensive compared to acquiring a standard X-ray scan. Therefore, in order to decrease patients' exposure to radiation and reduce time and cost, it would be highly desirable to be able to reconstruct volumetric CT data using just a few X-ray images. While such a reconstructed CT volume may not replace an actual CT volume for all purposes, it could be used for various purposes, such as for the purpose of segmenting anatomical structures.

BRIEF SUMMARY OF THE INVENTION

The present invention provides a method and system for automated computer-based reconstruction of 3D computed tomography (CT) volumes from a small number of X-ray radiographs. Embodiments of the present invention also automatically generate a 3D segmentation mask (or a 3D surface model) of an anatomical structure from the small number of X-ray radiographs.

In one embodiment of the present invention, a sparse 3D volume is generated from one or more X-ray images of a patient. A final reconstructed 3D CT volume is generated from the sparse 3D volume using a trained deep neural network. A 3D segmentation mask of a target object can be generated from the sparse 3D volume using the trained deep neural network.

These and other advantages of the invention will be apparent to those of ordinary skill in the art by reference to the following detailed description and the accompanying drawings.

DETAILED DESCRIPTION

Figure 1:
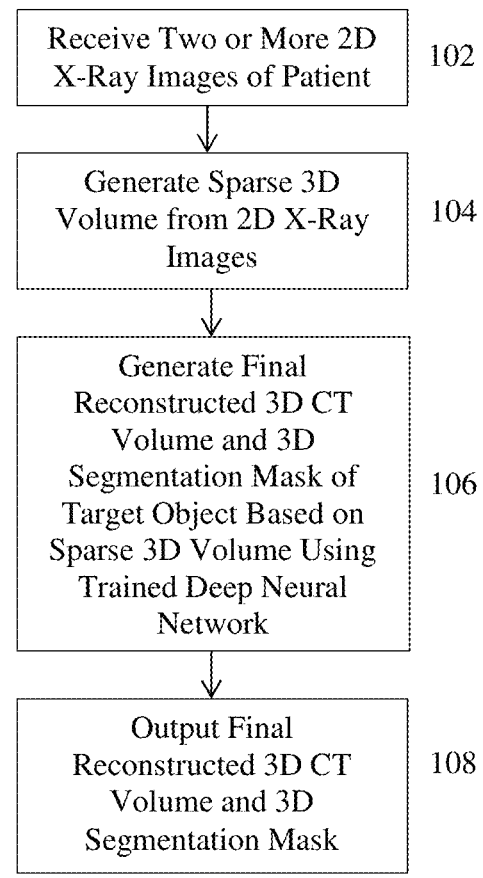
FIG. 1 illustrates a method for automated reconstruction of a 3D computed tomography (CT) volume and generation of a 3D segmentation mask from 2D X-ray images according to an embodiment of the present invention.

The present invention relates to a method and system for automated computer-based reconstruction of 3D computed tomography (CT) volumes and generation of 3D segmentation masks from a small number of X-ray radiographs. Embodiments of the present invention are described herein to give a visual understanding of the method for automated reconstruction of 3D CT volumes and generation of 3D segmentation masks. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide automated computer-based reconstruction of a 3D CT volume from a few 2D X-ray images. Accordingly, embodiments of the present invention provide automated reconstruction of 3D CT volumes with decreased patient exposure to radiation and reduced time and cost as compared to existing computer-based CT reconstruction techniques. Embodiments of the present invention also address the problem of automated generation of a segmentation mask (or 3D surface model) of anatomical structures of a patient. Such patient-specific models of anatomical structures are often used by surgeons during pre-operative surgery planning and also for image-based guidance during surgery. Existing approaches to constructing 3D surface models typically first use medical imaging techniques such as CT or magnetic resonance imaging (MRI), and then use segmentation algorithms (either manual or automatic). However, because of excessive time, cost, and/or radiation involved in CT and MRI, alternative approaches using only 2D X-ray radiographs have been proposed. Most of these approached use statistical shape models (SSMs). For example, in Zheng at al., "3D Reconstructions of a Patient-Specific Surface Model of the Proximal Femur from Calibrated X-ray Radiographs: A Validation Study," *Medical Physics*, Vol. 36, No. 4, 2009, pp. 1155-1166, iterative non-rigid registration of features extracted from an SSM to those interactively identified from the radiographs is performed. In Zheng et al., "Scaled, Patient-Specific 3D Vertebral Model Reconstruction Based on 2D Lateral Fluoroscopy," *International Journal of Computer Assisted Radiology and Surgery*, Vol. 6, No. 3, 2011, pp. 351-356, a semi-automatic method is proposed in which the user uses a segmentation tool to extract image contours. However, if the samples are significantly different, the method requires multiple SSMs. First the 2D/3D reconstruction problem is converted into a 3D/3D problem by computing the corresponding 3D point pairs, and then solved using a three stage iterative method. In Baka et al., "2D-3D Shape Reconstruction of the Distal Femur from Stereo X-ray Imaging Using Statistical Shape Models," *Medical Image Analysis*, Vol. 15, No. 6, 2011, pp. 840-850, an SSM-based method is proposed for pose estimation and shape reconstruction from two or more X-ray images involving manual initialization of the mean shape. In Schumann et al., "An Integrated System for 3D Hip Joint Reconstructions from 2D X-rays: A Preliminary Validation Study," *Annals of Biomedical Engineering*, Vol. 41, No. 10, 2013, pp. 2077-2087, the idea of using a motion calibration phantom to establish the correspondences between models is introduced. Registration of two different SSMs is performed—one from CT segmented surface models and the other being a hemi-pelvis SSM. The contours are extracted semi-automatically. In, Yu et al., "Fully Automatic Reconstruction of Personalized 3D Volumes of the Proximal Femur from 2D X-ray Images," *International Journal of Computer Assisted Radiology*, Vol. 11, No. 9, 2016, pp. 1673-1685, a fully automatic reconstruction method is proposed that uses a control point-based 2D-3D registration approach. This is a two-stage approach involving scaled-rigid registration and regularized deformable B-spline registration. A uniform 3D grid of points is placed on the 3D template and the registration transformation is calculated based on the transformations undergone by each point in the grid.

Embodiments of the present invention provide a fully automatic method that generates a 3D CT volume and a segmentation mask of an anatomical object given 2D X-ray images of the anatomical object. Embodiments of the present invention can perform the automatic reconstruction of the 3D CT volume and generation of the 3D segmentation mask from only a few 2D X-ray images. This is a very ill-posed problem, in the sense that one or two 2D X-ray images typically do not contain enough information that is required to generate the complete 3D volume. Accordingly, in order to tackle this problem, embodiments of the present invention cannot afford to not use any of the information available in the X-ray images. In existing techniques for computing 3D CT data, a large number of X-ray images (depending on the body part this number is typically anywhere from 100-750) are taken from various directions around the object. All of these 2D X-ray images are then "stitched" together by a tomographic reconstruction algorithm to produce the 3D CT volume data. In the problem addressed by embodiments of the present invention, instead of hundreds of X-ray images, very few X-ray images are available (e.g., less than four). Instead of using each these X-rays separately, embodiments of the present invention combine all of the available X-ray images using a tomographic reconstruction algorithm, such as filtered back projection (FBP), to obtain a sparse 3D CT volume which has all of the information contained in the input 2D X-ray images and also additional information of how the 2D X-ray images relate to one another. Once the sparse 3D CT volume is generated, it is passed through a trained deep neural network, such as a Conditional-Generative Adversarial Network, to generate the final reconstructed 3D CT volume along with the 3D segmentation mask.

FIG. 1 illustrates a method for automated reconstruction of a 3D CT volume and generation of a 3D segmentation mask from 2D X-ray images according to an embodiment of the present invention. The method of FIG. 1 transforms 2D X-ray images of a patient's anatomy to generate a reconstructed 3D CT volume and a 3D segmentation mask of a target object. The method of FIG. 1 requires only a small number of 2D X-ray images (radiographs) to perform the reconstruction of the 3D CT volume and the generation of the 3D segmentation mask. In particular, the method of FIG. 1 can be performed using a few as two 2D X-ray images of the patient.

Referring to FIG. 1, at step 102, two or more 2D X-ray images are received. The 2D X-ray images, also referred to as radiographs, are X-ray images of a target anatomical structure of a patient obtained with an X-ray scanner at different projection angles. The 2D X-ray images can be obtained using an X-ray scanner device, such as a stand-alone X-ray scanner, a CT scanner, or a C-arm CT scanner. The 2D X-ray images can be received directly from the X-ray scanner device or can be received by loading previously stored X-ray images of the patient from a memory or storage of a computer system or receiving the X-ray images via an electronic transmission from a remote computer system. According to an advantageous aspect of the present invention, the method of FIG. 1 can be performed with only a few (e.g., less than or equal to four) X-ray images, but the present invention is not limited thereto. At least two X-ray images are received. In an exemplary implementation, only two X-ray images (e.g., first and second X-ray images) may be received, but the present invention is not limited thereto.

At step 104, a sparse 3D volume is generated from the 2D X-ray images. In particular, the two or more 2D X-ray images are combined to using a tomographic reconstruction algorithm, such as filtered back-projection (FBP), to generate a sparse 3D volume which has all of the information contained in the input 2D X-ray images and also the additional information of how the input 2D X-ray images relate to each other. This additional information comes from the physical principles involved in the CT data computation by tomographic reconstruction and from the pose information of each of the 2D X-ray images. In some embodiments, such as when the X-ray images are generated using a CT scanner or C-arm CT scanner, the pose information for each 2D X-ray image is provided by the image acquisition device and is therefore readily available for the tomographic reconstruction algorithm. In other embodiments in which the pose information is not available from the image acquisition device, the relative poses of the 2D X-ray images can be estimated. In an exemplary embodiment, this pose estimation can be performed using a separate trained deep neural network that is trained to take the 2D X-ray images as inputs and output the pose parameters. In an exemplary implementation, FBP can be used to generate the sparse 3D volume from the two or more 2D X-ray images. FBP is a well known tomographic reconstruction algorithm. However, the present invention is not limited to filtered back-projection, and other tomographic reconstruction algorithms can be used as well.

At step 106, a final reconstructed 3D CT volume and a 3D segmentation mask of a target object is generated from the sparse 3D volume using a trained deep neural network. Once the sparse 3D volume is generated (in step 104), the sparse 3D volume is input to and passed through a trained deep neural network to generate the final reconstructed 3D CT volume along with the 3D segmentation mask. The final reconstructed CT volume is a non-sparse CT volume that will appear as if it was reconstructed from a full set of X-ray projection images. The 3D segmentation mask is a 3D mask showing the voxels in the final reconstructed CT volume that are within a boundary of a target object, such as a organ, vessel, bone structure, or other anatomical structure.

In an advantageous embodiment, the deep neural network is a deep image-to-image network (DI2IN) and the network architecture has an encoder and decoder. For example, the DI2IN can have a deep convolutional encoder-decoder network architecture. The encoder has a series of layers that code the sparse 3D input information into a code whose size is substantially less than the size of the input sparse 3D volume. The decoder has a series of layers that will then decode the code into the outputs of the final reconstructed 3D volume and the 3D segmentation mask. All the intermediate information generated in the encoder is shared with the decoder, so that no information is lost in the encoding process. In one exemplary implementation, the network architecture can include a single decoder with multiple outputs to output the final reconstructed 3D CT volume and the 3D segmentation mask. In another exemplary implementation, the network architecture can include a single encoder and two decoders, one trained to output the final reconstructed 3D volume and the other trained to output the 3D segmentation mask. An objective function based on the distance between the generated output of the deep neural network and the real ground truth reconstructed CT volumes and 3D segmentation masks in training data is used to train the deep neural network to learn the weights for the layers of the encoder and the decoder. In an advantageous embodiment, the deep neural network can be a generative adversarial network or a conditional-generative adversarial network. In this case, a discriminator network is used together with the DI2IN during training. The discriminator network judges the output of the DI2IN and decides whether the output looks close enough to the real ground truth training data. The advantage of the discriminator is that it adds an additional constraint to the DI2IN during training which helps the output of the DI2IN (i.e., the final reconstructed 3D CT volume and the 3D segmentation mask) look as close to the real ground truth data as possible.

Figure 2:
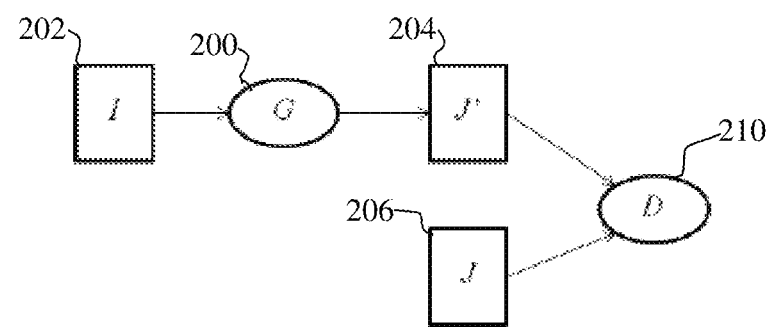
FIG. 2 illustrates a generative adversarial network for generating a fully reconstructed 3D CT volume from an input sparse 3D volume according to an embodiment of the present invention.

In an exemplary embodiment, the deep neural network is trained as a generative adversarial network. FIG. 2 illustrates a generative adversarial network for generating a fully reconstructed 3D CT volume from an input sparse 3D volume according to an embodiment of the present invention. As shown in FIG. 2, a sparse 3D volume I 202 is input to a generator G 200. The generator G 200 is a deep neural network, such as a DI2IN implemented using a convolutional encoder-decoder architecture, that generates a synthesized fully reconstructed 3D CT volume J' 204. The synthesized fully reconstructed 3D CT volume J' 204 and a ground truth fully reconstructed 3D CT volume J 206 are input to a discriminator D 210. The discriminator D 210 is another deep neural network that distinguishes between the synthesized volume J' 204 and the real volume J 206. During training, the generator G 200 and the discriminator D 210 together play the following minimax game:

$$\min_G \max_D E_{J \sim p(J)}[\log(D(J))] + E_{I \sim p(I)}[\log(1 - D(J' = G(I)))].  \quad (1)$$

The networks are trained end-to-end by iteratively adjusting the parameters (weights) of the discriminator D 210 and the generator G 200 to optimize Equation (1). In Equation (1), the first term is a cost related to the real sample J 206 and the second term is a cost related to the synthesized sample J' 204. The discriminator D 210 maximizes the function (i.e., trying its best to distinguish between the real and synthesized samples) and the generator G 200 minimizes the function (i.e., synthesize real looking samples to fool the discriminator). The generator G 200 and the discriminator D 210 evolve dynamically in the sense of learning better network parameters until they reach equilibrium, that is, the synthesized volume J' 204 becomes as close as possible from being indistinguishable from the real volume J 206 through the eyes of the discriminator D 210. The trained generator G 200 (i.e., DI2IN) is then stored, for example, in a memory or storage of a computer system and used alone for inference (in step 106) in order to generate a synthesized fully reconstructed CT volume from an input sparse 3D volume.

It is to be understood that although FIG. 2 is described herein for a synthesized output image J' of a fully reconstructed CT volume, FIG. 2 can be similarly applied to a target output image J' of a 3D segmentation mask. In a possible implementation in which the generator G generates both a synthesized fully reconstructed 3D CT volume and a 3D segmentation mask, the generative adversarial network shown in FIG. 2 can be extended to have two discriminators, one which distinguishes between synthesized and real fully reconstructed 3D CT volumes and another which distinguishes between synthesized and real (ground-truth) 3D segmentation masks. In this case, the function in Equation (1) can be extended to include error terms for both discriminators and the minimax game used for training can be played together by all three networks.

Figure 3:
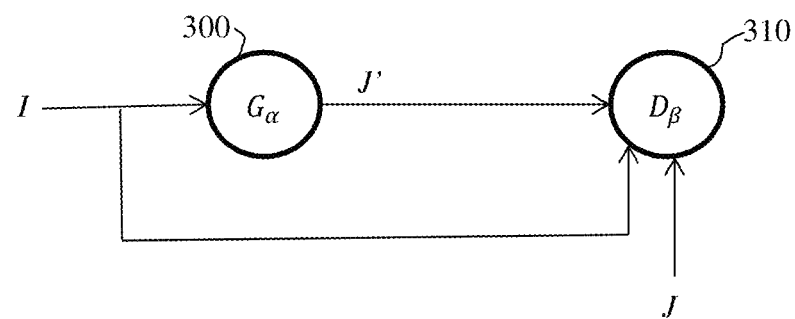
FIG. 3 illustrates a conditional-generative adversarial network for generating a fully reconstructed 3D CT volume from an input sparse 3D volume according to an embodiment of the present invention.

In another possible embodiment, the deep neural network can be trained as a conditional-generative adversarial network. In a conditional-generative adversarial network, the discriminator is conditioned on the input image I. FIG. 3 illustrates a conditional-generative adversarial network for generating a fully reconstructed 3D CT volume from an input sparse 3D volume according to an embodiment of the present invention. As shown in FIG. 3, a sparse 3D volume I is input to a generator $G_\alpha$ 300. The generator $G_\alpha$ 300 is a deep neural network, such as a DI2IN, that generates a synthesized fully reconstructed 3D CT volume I' from the input sparse 3D volume I. The input sparse 3D volume I, the synthesized fully reconstructed 3D CT volume J', and a real fully reconstructed 3D CT volume J are input to a discriminator $D_\beta$ 310. The discriminator $D_\beta$ 310 is another deep neural network that distinguishes between the synthesized volume I' and the real volume J. During training, the generator $G_\alpha$ 300 and the discriminator $D_\beta$ 310 together play the following minimax game, conditioned on the input sparse 3D volume I:

$$\min_\alpha \max_\beta E_{I,J \sim p(I,J)}[\log(D_\beta(J|I))] + E_{I,J \sim p(I,J)}[\log(1 - D_\beta(J' = G_\alpha(i)|I))], \quad (2)$$

where $\alpha$ and $\beta$ are the parameters (weights) of the generator $G_\alpha$ 300 and the discriminator $D_\beta$, respectively. The networks are trained end-to-end by iteratively adjusting the parameters (weights) $\alpha$ and $\beta$ to optimize Equation (2). In Equation (2), the first term is a cost related to the real sample J and the second term is a cost related to the synthesized sample J'. The generator $G_\alpha$ 300 and the discriminator $D_\beta$ 310 evolve dynamically in the sense of learning better network parameters until they reach equilibrium, that is, the synthesized volume J'=$G_\alpha$(I) becomes indistinguishable from the real volume J through the eyes of the discriminator N 310. Under such circumstances, the generator $G_\alpha$ 300 actually generates the real fully reconstructed 3D CT volume for the input sparse 3D volume I. The trained generator $G_\alpha$ 300 (i.e., DI2IN) is then stored, for example, in a memory or storage of a computer system and used alone for inference (in step 106) in order to generate a synthesized fully reconstructed CT volume from an input sparse 3D volume.

It is to be understood that although FIG. 3 is described herein for a synthesized output image J' of a fully reconstructed CT volume, FIG. 3 can be similarly applied to a target output image J' of a 3D segmentation mask. In a possible implementation in which the generator G generates both a synthesized fully reconstructed 3D CT volume and a 3D segmentation mask, the conditional-generative adversarial network shown in FIG. 3 can be extended to have two discriminators, one which distinguishes between synthesized and real fully reconstructed 3D CT volumes, conditioned on the input sparse 3D volume, and another which distinguishes between synthesized and real (ground-truth) 3D segmentation masks, conditioned on the input sparse 3D volume. In this case, the function in Equation (2) can be extended to include error terms for both discriminators and the minimax game used for training can be played together by all three networks.

Figure 4:
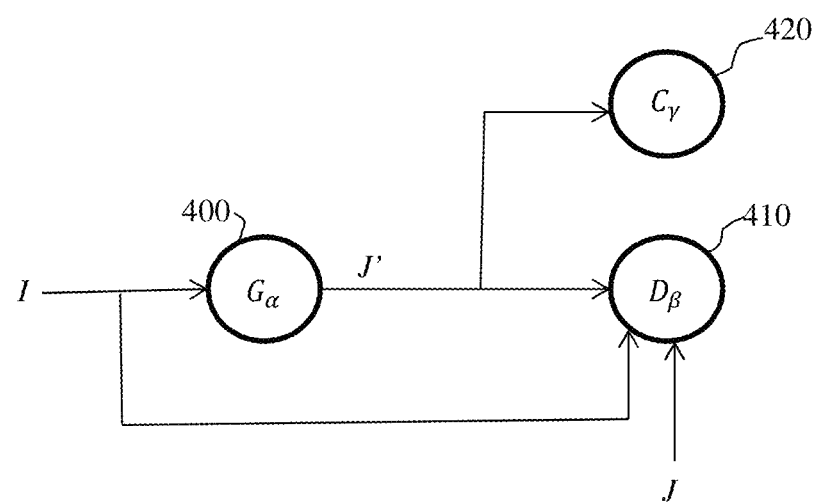
FIG. 4 illustrates a conditional-generative adversarial network coupled with a voxel-wise cost function according to an embodiment of the present invention.

In an advantageous embodiment of the present invention, the training can integrate a voxel-wise cost function with the conditional-generative adversarial network framework. FIG. 4 illustrates a conditional-generative adversarial network coupled with a voxel-wise cost function according to an embodiment of the present invention. As shown in FIG. 4, a sparse 3D volume I is input to a generator $G_\alpha$ 400. The generator $G_\alpha$ 400 is a deep neural network, such as a DI2IN, that generates a synthesized fully reconstructed 3D CT volume I' from the input sparse 3D volume I. The input sparse 3D volume I, the synthesized fully reconstructed 3D CT volume J', and a real (ground truth) fully reconstructed 3D CT volume J are input to a discriminator $D_\beta$ 410. The discriminator $D_\beta$ 410 is another deep neural network that distinguishes between the synthesized volume J' and the real volume J. In addition to being input to the discriminator $D_\beta$ 410, the synthesized fully reconstructed 3D CT volume J' is also input to a cost function $C_\gamma$ 420 having parameters γ. The cost function $C_\gamma$ 420 compares the synthesized fully reconstructed 3D CT volume J' for a given input sparse 3D volume I with the ground-truth fully reconstructed 3D CT volume J for that input sparse 3D volume I. In an exemplary implementation, the cost function $C_\gamma$ 420 computes a voxel-wise error/distance between the synthesize volume I' and the ground truth volume J. For example, the cost function $C_\gamma$ 420 may be implemented using a regressive or logistic function.

During training, the parameters α of the generator $G_\alpha$ 300 and the parameters β of the discriminator $D_\beta$ 310 are learned to optimize the following minimax game, conditioned on the input sparse 3D volume I:

$$\min_\alpha \max_\beta E_{I,J\sim p(I,J)}[C_\gamma(J,J'=G_\alpha(I)|I)]+E_{I,J\sim p(I,J)}[\log(D_\beta(J|I)]+E_{I,J\sim p(I,J)}[\log(1-D_\beta(J'=G_\alpha(I)|I)]. \quad (3)$$

In Equation (3), the first term is a cost computed by the cost function $C_\gamma$ 420, the second term cost related to the classification of the real sample J by the discriminator $D_\beta$ 410, and the third term is a cost related to the classification of the synthesized sample I' by the discriminator $D_\beta$ 410. Given a set of N training pairs $\{(I_n, J_n)\}$, the task in training is to learn parameters α and β that yield the solution to the following cost function in which the expectation value is replaced by the sample average over the set of training samples:

$$\min_\alpha \max_\beta \frac{1}{N}\sum_{n=1}^{N}[C_\gamma(J_n, J'_n = G_\alpha(I_n)|I_n) + \log(D_\beta(J_n|I_n)) + \log(1-D_\beta(J'_n = G_\alpha(I_n)|I_n))]. \quad (4)$$

In the embodiment described herein using the cost function in Equation (4), the parameters γ of the cost function $C_\gamma$ 420 are preset and not adjusted in the training. In another possible implementation, depending of the formulation of the cost function $C_\gamma$ 420, the parameters γ can also be adjusted together with the parameters α and β during training to optimize the cost function.

The parameters α and β that optimize the cost function in Equation (4) are learned by iteratively alternating the following two steps until the parameters α and β converge (or until a preset maximum number of training iterations is reached):

Step 1—With the parameters α of the generator $G_\alpha$ 400 fixed, solve the following maximization task for the parameters β of the discriminator $D_\beta$ 410:

$$\max_\beta \frac{1}{N}\sum_{n=1}^{N}[\log(D_\beta(J_n|I_n))+\log(1-D_\beta(J'_n=G_\alpha(I_n)|I_n))].$$

In the advantageous implementation, in which a deep neural network is used to model the discriminator $D_\beta$ 410, a backpropagation step can be implemented based on a minibatch of training pairs in order to perform this maximization task.

Step 2—With the β of the discriminator $D_\beta$ 410 fixed, solve the following minimization task for the parameters α of the generator $G_\alpha$ 400:

$$\min_\alpha \frac{1}{N}\sum_{n=1}^{N}[C_\gamma(J_n, J'_n = G_\alpha(I_n)|I_n)+\log(1-D_\beta(J'_n=G_\alpha(I_n)|I_n))].$$

It is practically found that, rather than training $G_\alpha$ 400 to minimize $\log(1-D_\beta(J'))$, training $G_\alpha$ 400 to maximize $\log(D_\beta(J'))$ leads to better gradient signals early in learning, even though both objective functions yield the same fixed point. Accordingly, in an advantageous implementation, the parameters α of the generator $G_\alpha$ 400 can be learned in step 2 using the following minimization problem:

$$\min_\alpha \frac{1}{N}\sum_{n=1}^{N}[C_\gamma(J_n, J'_n = G_\alpha(I_n)|I_n)-\log(D_\beta(J'_n=G_\alpha(I_n)|I_n))].$$

In the advantageous implementation, in which a deep neural network (e.g. DI2IN) is used to model the discriminator $D_\beta$ 410, a backpropagation step can be implemented based on a minibatch of training pairs in order to perform this minimization task.

Once the training is complete, the trained generator G 400 (i.e., DI2IN) is then stored, for example, in a memory or storage of a computer system and used alone for inference (in step 106) in order to generate a synthesized fully reconstructed CT volume from an input sparse 3D volume. It is to be understood that although FIG. 4 is described herein for a synthesized output image J' of a fully reconstructed CT volume, FIG. 4 can be similarly applied to a target output image J' of a 3D segmentation mask. In a possible implementation in which the generator G generates both a synthesized fully reconstructed 3D CT volume and a 3D segmentation mask, the conditional-generative adversarial network shown in FIG. 4 can be extended to have two discriminators, one which distinguishes between synthesized and real fully reconstructed 3D CT volumes and another which distinguishes between synthesized and real (ground-truth) 3D segmentation masks, and two voxel-wise cost functions, one that compares synthesized and ground-truth fully reconstructed 3D CT volumes and another that compares synthesized and ground-truth 3D segmentation masks. In this case, the functions in Equations (3) and (4) can be extended to include error terms for both discriminators and both cost functions, and the training to learn the network parameters can be iteratively alternate between all three networks.

Returning to FIG. 1, at step 108, the final reconstructed 3D CT image and the 3D segmentation mask of the target object are output. The final reconstructed 3D CT image and the 3D segmentation mask of the target object can be output by displaying the final reconstructed 3D CT image and the 3D segmentation mask of the target object on a display device of a computer system. For example, the final reconstructed 3D CT image and/or the 3D segmentation mask of the target object can be displayed on a displayed device as a 3D visualization or by displaying various 2D slices extracted from the final reconstructed 3D CT image and/or the 3D segmentation mask of the target object.

Figure 5:
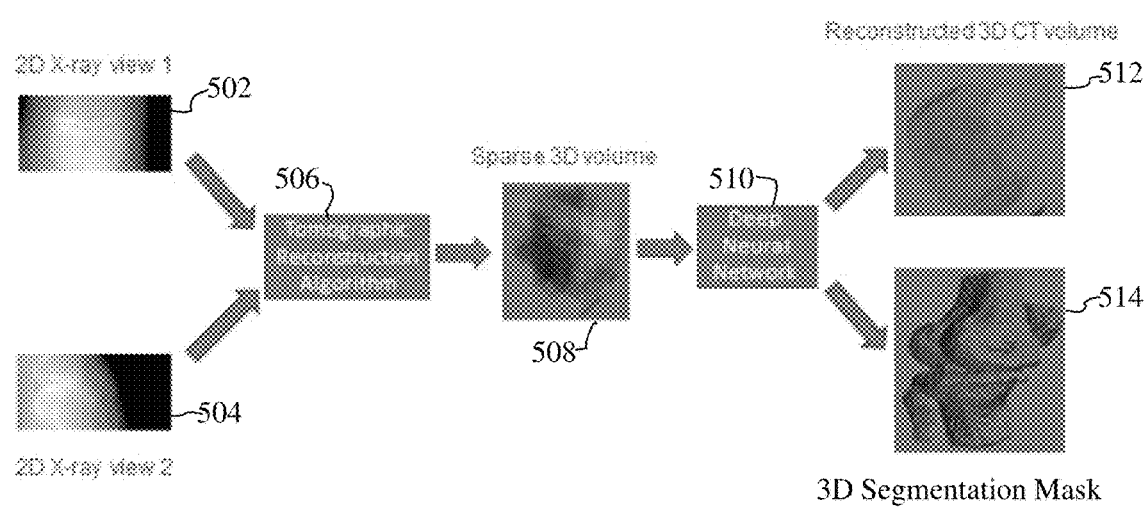
FIG. 5 illustrates an overview of the method of FIG. 1 and exemplary results of the method of FIG. 1.

FIG. 5 illustrates an overview of the method of FIG. 1 and exemplary results of the method of FIG. 1. As shown in FIG. 5, a first 2D X-ray view 502 and a second 2D x-ray view 504 are obtained for a patient. A tomographic reconstruction algorithm 506, such as FBP, is used to generate a sparse 3D volume 508 from the first and second X-ray views 502 and 504. The sparse 3D volume 508 is input to a trained deep neural network 510, and the trained deep neural network 510 generates a final reconstructed 3D CT volume 512 and a 3D segmentation mask 514 of a target object. In the exemplary results shown in FIG. 5, the target object is the bone structures in the knee. Accordingly, the reconstructed 3D segmentation mask 514 is a reconstructed 3D bone mask of the knee.

In the embodiment of FIG. 1, a final reconstructed 3D CT image and a 3D segmentation mask are generated from two or more 2D x-ray images of a patient. In an alternative embodiment, a final reconstructed 3D CT image and/or a 3D segmentation mask can be similarly generated using a single 2D x-ray image. In this case, a second x-ray image at a different pose is first estimated based on the single x-ray image using a trained deep image-to-image neural network. Then, the tomographic reconstruction algorithm is used to generate a sparse 3D volume from the original x-ray image of the patient and the estimated second x-ray image. This sparse 3D volume is then input to a trained deep neural network, which generates the final reconstructed 3D CT volume and the 3D segmentation mask based on the sparse 3D volume as described above in step 106 of FIG. 1.

The method of FIG. 1 described above generates a final reconstructed 3D CT volume from a small number of x-ray images. This method may be similarly applied to reconstruct 3D volumes of medical imaging other than CT. Depending on the image modality to be reconstructed, a suitable sparse reconstruction can first be generates based on the physical principles involved in that particular imaging modality, and then a trained deep neural network can be used to generate the target reconstructed 3D outputs from the sparse reconstruction.

Figure 6:
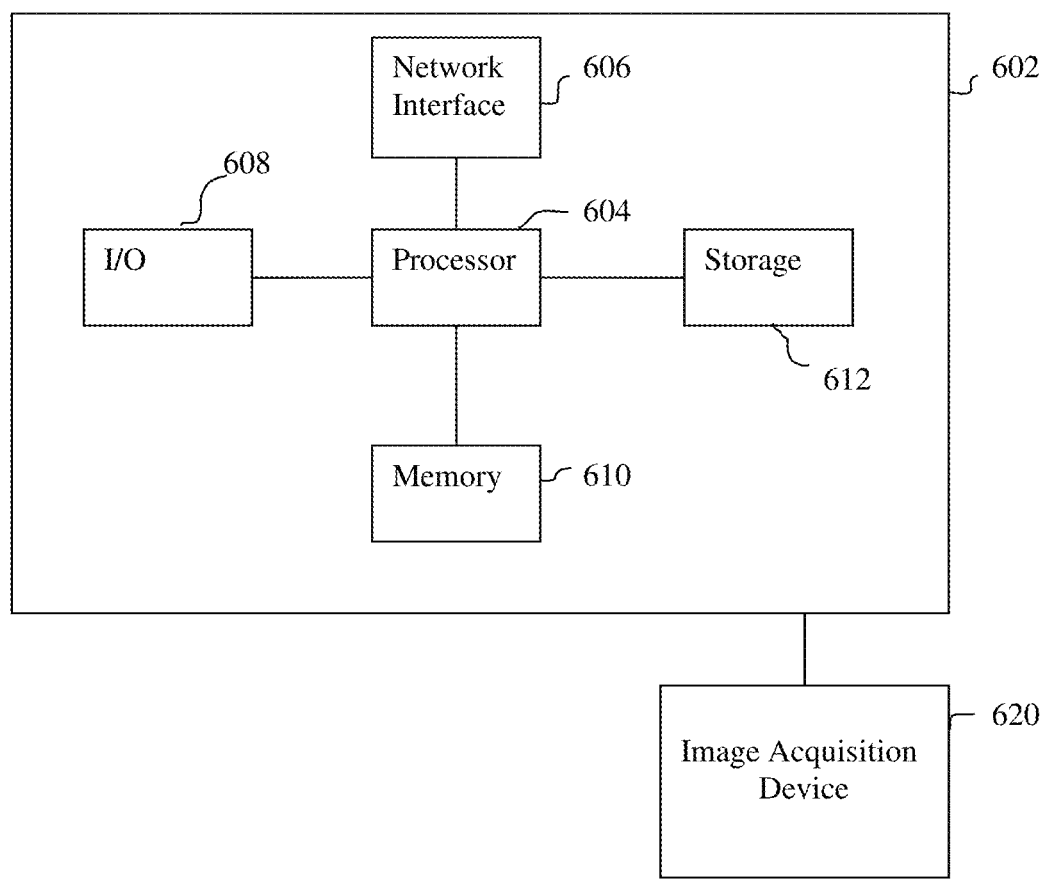
FIG. 6 is a high-level block diagram of a computer capable of implementing the present invention.

The above-described method for automated reconstruction of a 3D CT volume and generation of a 3D segmentation mask from 2D X-ray images may be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the method of FIG. 1 may be defined by the computer program instructions stored in the memory 610 and/or storage 612 and controlled by the processor 604 executing the computer program instructions. An image acquisition device 620, such as a CT scanner, C-arm CT scanner, or X-ray scanner, can be connected to the computer 602 to input image data to the computer 602. It is possible to implement the image acquisition device 620 and the computer 602 as one device. It is also possible that the image acquisition device 620 and the computer 602 communicate wirelessly through a network. In a possible embodiment, the computer 602 can be located remotely with respect to the image acquisition device 620 and the method steps described herein can be performed as part of a server or cloud based service. In this case, the method steps may be performed on a single computer or distributed between multiple networked computers. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate images/volumes received from the image acquisition device 620. One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automated reconstruction of a 3D computed tomography (CT) volume one or more X-ray images, comprising:
   generating a sparse 3D volume from one or more X-ray images of a patient; and
   generating a final reconstructed 3D CT volume from the sparse 3D volume using a trained deep neural network.

2. The method of claim 1, wherein the one or more X-ray images of the patient comprise a first x-ray image and a second x-ray image, and generating the sparse 3D volume from the one or more X-ray images of the patient comprises:
   generating the sparse 3D volume from the first X-ray image and the second X-ray image using a tomographic reconstruction algorithm.

3. The method of claim 2, wherein the one or more x-ray images of the patient comprise only the first and second x-ray images, and generating the sparse 3D volume from the first X-ray image and the second X-ray image using a tomographic reconstruction algorithm comprises:
   generating the sparse 3D volume from the first X-ray image and the second X-ray image without any additional x-ray images using a tomographic reconstruction algorithm.

4. The method of claim 1, further comprising:
generating a 3D segmentation mask of a target object from the sparse 3D volume using the trained deep neural network.

5. The method of claim 4, wherein the trained deep neural network is a multi-output deep image-to-image network having encoder layers that code the sparse 3D volume into a code whose size is smaller than the spare 3D volume and decoder layers that decode the code into the final reconstructed 3D volume and the 3D segmentation mask of the target object.

6. The method of claim 1, wherein the trained deep neural network is a deep image-to-image network that is trained in a generative adversarial network together with a discriminator network for distinguishing between synthesized reconstructed 3D CT volumes generated by the deep image-to-image network from input sparse 3D volume training samples and real reconstructed 3D CT volume training samples.

7. The method of claim 1, wherein the trained deep neural network is a deep image-to-image network that is trained in a conditional-generative adversarial network together with a discriminator network for distinguishing between synthesized reconstructed 3D CT volumes generated by the deep image-to-image network from input sparse 3D volume training samples and real reconstructed 3D CT volume training samples, conditioned on the input sparse 3D volume training samples.

8. The method of claim 7, wherein the conditional-generative adversarial network is integrated with a voxel-wise cost function that computes a voxel-wise error between the synthesized reconstructed 3D CT volumes generated by the deep image-to-image network from input sparse 3D volume training samples and corresponding ground-truth reconstructed 3D CT volume training samples, and the deep image-to-image network and the discriminator network are trained together to optimize, over a plurality of training samples, a minimax objective function that includes a first term that calculates an error using the voxel-wise cost function, a second term that calculates an error of the discriminator network classifying the real reconstructed 3D CT training samples, and a third term that calculates and error of the discriminator network classifying the synthesized reconstructed 3D CT volumes generated by the deep image-to-image network.

9. An apparatus for automated reconstruction of a 3D computed tomography (CT) volume one or more X-ray images, comprising:
means for generating a sparse 3D volume from one or more X-ray images of a patient; and
means for generating a final reconstructed 3D CT volume from the sparse 3D volume using a trained deep neural network.

10. The apparatus of claim 9, further comprising:
means for generating a 3D segmentation mask of a target object from the sparse 3D volume using the trained deep neural network.

11. The apparatus of claim 9, wherein the trained deep neural network is a deep image-to-image network that is trained in a generative adversarial network together with a discriminator network for distinguishing between synthesized reconstructed 3D CT volumes generated by the deep image-to-image network from input sparse 3D volume training samples and real reconstructed 3D CT volume training samples.

12. The apparatus of claim 9, wherein the trained deep neural network is a deep image-to-image network that is trained in a conditional-generative adversarial network together with a discriminator network for distinguishing between synthesized reconstructed 3D CT volumes generated by the deep image-to-image network from input sparse 3D volume training samples and real reconstructed 3D CT volume training samples, conditioned on the input sparse 3D volume training samples.

13. The apparatus of claim 12, wherein the conditional-generative adversarial network is integrated with a voxel-wise cost function that computes a voxel-wise error between the synthesized reconstructed 3D CT volumes generated by the deep image-to-image network from input sparse 3D volume training samples and corresponding ground-truth reconstructed 3D CT volume training samples, and the deep image-to-image network and the discriminator network are trained together to optimize, over a plurality of training samples, a minimax objective function that includes a first term that calculates an error using the voxel-wise cost function, a second term that calculates an error of the discriminator network classifying the real reconstructed 3D CT training samples, and a third term that calculates and error of the discriminator network classifying the synthesized reconstructed 3D CT volumes generated by the deep image-to-image network.

14. A non-transitory computer-readable medium storing computer program instructions for automated reconstruction of a 3D computed tomography (CT) volume one or more X-ray images, the computer program instructions when executed by a processor cause the processor to perform operations comprising:
generating a sparse 3D volume from one or more X-ray images of a patient; and
generating a final reconstructed 3D CT volume from the sparse 3D volume using a trained deep neural network.

15. The non-transitory computer-readable medium of claim 14, wherein the one or more X-ray images of the patient comprise a first x-ray image and a second x-ray image, and generating the sparse 3D volume from the one or more X-ray images of the patient comprises:
generating the sparse 3D volume from the first X-ray image and the second X-ray image using a tomographic reconstruction algorithm.

16. The non-transitory computer-readable medium of claim 14, wherein the operations further comprise:
generating a 3D segmentation mask of a target object from the sparse 3D volume using the trained deep neural network.

17. The non-transitory computer-readable medium of claim 16, wherein the trained deep neural network is a multi-output deep image-to-image network having encoder layers that code the sparse 3D volume into a code whose size is smaller than the spare 3D volume and decoder layers that decode the code into the final reconstructed 3D volume and the 3D segmentation mask of the target object.

18. The non-transitory computer-readable medium of claim 14, wherein the trained deep neural network is a deep image-to-image network that is trained in a generative adversarial network together with a discriminator network for distinguishing between synthesized reconstructed 3D CT volumes generated by the deep image-to-image network from input sparse 3D volume training samples and real reconstructed 3D CT volume training samples.

19. The non-transitory computer-readable medium of claim 14, wherein the trained deep neural network is a deep image-to-image network that is trained in a conditional-generative adversarial network together with a discriminator network for distinguishing between synthesized reconstructed 3D CT volumes generated by the deep image-to-image network from input sparse 3D volume training samples and real reconstructed 3D CT volume training samples, conditioned on the input sparse 3D volume training samples.

20. The non-transitory computer-readable medium of claim 19, wherein the conditional-generative adversarial network is integrated with a voxel-wise cost function that computes a voxel-wise error between the synthesized reconstructed 3D CT volumes generated by the deep image-to-image network from input sparse 3D volume training samples and corresponding ground-truth reconstructed 3D CT volume training samples, and the deep image-to-image network and the discriminator network are trained together to optimize, over a plurality of training samples, a minimax objective function that includes a first term that calculates an error using the voxel-wise cost function, a second term that calculates an error of the discriminator network classifying the real reconstructed 3D CT training samples, and a third term that calculates and error of the discriminator network classifying the synthesized reconstructed 3D CT volumes generated by the deep image-to-image network.

* * * * *